US011345929B2

(12) United States Patent
Wang

(10) Patent No.: US 11,345,929 B2
(45) Date of Patent: *May 31, 2022

(54) METHODS FOR ANALYSIS OF VIRAL CAPSID PROTEIN COMPOSITION

(71) Applicant: Regeneron Pharmaceuticals, Inc., Tarrytown, NY (US)

(72) Inventor: Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/663,109

(22) Filed: Oct. 24, 2019

(65) Prior Publication Data

US 2020/0131533 A1 Apr. 30, 2020

Related U.S. Application Data

(60) Provisional application No. 62/750,583, filed on Oct. 25, 2018.

(51) Int. Cl.
| | |
|---|---|
| *C12N 15/86* | (2006.01) |
| *C12N 7/00* | (2006.01) |
| *G01N 30/02* | (2006.01) |
| *C07K 1/20* | (2006.01) |
| *G01N 30/06* | (2006.01) |

(52) U.S. Cl.
CPC .............. *C12N 15/86* (2013.01); *C12N 7/00* (2013.01); *G01N 30/02* (2013.01); *C07K 1/20* (2013.01); *C12N 2710/14143* (2013.01); *C12N 2750/14142* (2013.01); *C12N 2750/14143* (2013.01); *C12N 2750/14152* (2013.01); *G01N 2030/027* (2013.01); *G01N 2030/062* (2013.01)

(58) Field of Classification Search
CPC ................ C12N 15/86; C12N 7/00; C12N 2710/14143; C12N 2750/14142; C12N 2750/14143; C12N 2750/14152; G01N 30/02; G01N 2030/027; G01N 2030/062; G01N 33/6848; G01N 33/6803; G01N 30/7233; C07K 1/20; C07K 16/2896; C12Y 302/0102
See application file for complete search history.

(56) References Cited

U.S. PATENT DOCUMENTS 8,946,395 B1 * 2/2015 Herigstad ................ C07K 1/20
530/412

FOREIGN PATENT DOCUMENTS

WO 2018/035059 A1 2/2018

OTHER PUBLICATIONS

Wang S, Liu AP, Yan Y, Daly TJ, Li N. Characterization of product-related low molecular weight impurities in therapeutic monoclonal antibodies using hydrophilic interaction chromatography coupled with mass spectrometry. J Pharm Biomed Anal. May 30, 2018;154:468-475. Epub Mar. 16, 2018. (Year: 2018).*
Michen B, Graule T. Isoelectric points of viruses. J Appl Microbiol. Aug. 2010;109(2):388-97. Epub Jan. 22, 2010. (Year: 2010).*
Potter M, Lins B, Mietzsch M, Heilbronn R, Van Vliet K, Chipman P, Agbandje-McKenna M, Cleaver BD, Clément N, Byrne BJ, Zolotukhin S. A simplified purification protocol for recombinant adeno-associated virus vectors. Mol Ther Methods Clin Dev. Aug. 13, 2014;1:14034. (Year: 2014).*
P. Gagnon, E. Grund, T. Lindback. Large-scale process development for hydrophobic interaction chromatography, part 2: controlling process variation. Biopharm, 8 (1995), pp. 36-41. (Year: 1995).*
P. Gagnon, E. Grund, T. Lindback. Large scale process development for hydrophobic interaction chromatography, part 1: gel selection and development of binding conditions. Biopharm, 8 (1995), pp. 21-27. (Year: 1995).*
Weigel T, Soliman R, Wolff MW, Reichl U. Hydrophobic-interaction chromatography for purification of influenza A and B virus. J Chromatogr B Analyt Technol Biomed Life Sci. Jun. 1, 2019;1117:103-117. Epub Apr. 1, 2019. (Year: 2019).*
Wolff MW, Siewert C, Hansen SP, Faber R, Reichl U. Purification of cell culture-derived modified vaccinia ankara virus by pseudo-affinity membrane adsorbers and hydrophobic interaction chromatography. Biotechnol Bioeng. Oct. 1, 2010;107(2):312-20. (Year: 2010).*
Li H, Yang Y, Zhang Y, Zhang S, Zhao Q, Zhu Y, Zou X, Yu M, Ma G, Su Z. A hydrophobic interaction chromatography strategy for purification of inactivated foot-and-mouth disease virus. Protein Expr Purif. Sep. 2015;113:23-9. Epub May 6, 2015. (Year: 2015).*
Sviben D, Forcic D, et al. Recovery of infective virus particles in ion-exchange and hydrophobic interaction monolith chromatography is influenced by particle charge and total-to-infective particle ratio. J Chromatogr B Analyt Technol Biomed Life Sci. Jun. 1, 2017;1054:10-19. Epub Apr. 8, 2017. (Year: 2017).*
Liu AP, Patel SK, Xing T, Yan Y, Wang S, Li N. Characterization of Adeno-Associated Virus Capsid Proteins Using Hydrophilic Interaction Chromatography Coupled with Mass Spectrometry. J Pharm Biomed Anal. Sep. 10, 2020;189:113481. Epub Jul. 21, 2020. (Year: 2020).*
Shytuhina Anastasija et al., "Development and application of a reversed-phase high-performance liquid chromatographic method for quantitation and characterization of a Chikungunya virus-like particle vaccine," Journal of Chromatography A., Elsevier Amsterdam, NL, vol. 1364, Jun. 19, 2014, pp. 192-197.
Marco Benevento et al.: "Adenovirus Composition, Proteolysis, and Disassembly Studied by In-depth Qualitative and Quantitative Proteomics," Journal of Biological Chemistry, vol. 289, No. 16, Mar. 3, 2014, pp. 11421-11430.
International Search Report PCT Application No. PCT/US2019/057936, International Filing Date Oct. 24, 2019, dated Jan. 31, 2020.

* cited by examiner

*Primary Examiner* — Rachel B Gill
(74) *Attorney, Agent, or Firm* — Kramer Levin Naftalis & Frankel LLP

(57) ABSTRACT

Methods of determining the stoichiometry of a viral capsid and/or determining the heterogeneity of protein components in a viral capsid are disclosed.

20 Claims, 6 Drawing Sheets

VP1  VP2  VP3
34 46 115 139 161 261 266 328 381 447 449 459 522 534 553 573 584 587 588 591 664

M.W. of VP1 ~ 81.5 kDa
M.W. of VP2 ~ 66.4 kDa
M.W. of VP3 ~ 59.9 kDa

METHODS FOR ANALYSIS OF VIRAL CAPSID PROTEIN COMPOSITION

CROSS-REFERENCE TO RELATED APPLICATIONS

This application claims the benefit under 35 USC § 119(e) of U.S. Provisional Application No. 62/750,583, filed Oct. 25, 2018, which is incorporated herein by reference in its entirety for all purposes.

FIELD OF THE INVENTION

The present invention pertains to methods for determining the heterogeneity of a viral particle, such as an adeno-associated virus (AAV) particle using hydrophilic interaction liquid chromatography (HILIC) and mass spectrometry determination.

BACKGROUND

Gene therapy has emerged as an alternative treatment for genetic diseases. Gene therapy involves the transfer of some genetic material (DNA, RNA or oligonucleotides) into target cells. In practice, the gene of interest (also called a transgene) must be delivered to the cell by a vector, which carries a molecule of DNA or RNA. It is based on the transfer of functional genes to replace or supplement defective genes. The transgene can be delivered into the cell by the vector. The method of delivery differs depending on the type of treatment and organ/tissue to be targeted.

Viral particles have emerged as vectors for gene therapy and the treatment of disease. Viral vectors, such as those based on the genome of adeno-associated virus (AAV), offer exciting platforms for gene delivery. Currently, 12 human serotypes of AAV (AAV1-12) have been described, many of which have distinct cell and tissue tropism, potentially creating the option to generate a variety of different vector classes from this viral genus.

However, one of the problems facing the adoption of viral vectors in gene therapy is the characterization of viral particle homogeneity. While classic techniques such as electron microscopy and Southern Blots can characterize viral particle heterogeneity, such as AAV heterogeneity and aggregation, they do not provide sufficient resolution for quantifying homogeneity when it comes to producing clinical-grade viral vector preparations. Complete characterization of the constituent viral capsid proteins, such as the capsid proteins of AAV vectors, including their sequences and post-translational modifications (PTMs), is highly recommended to ensure product quality and consistency. Thus, methods are needed to determine the homogeneity of viral particles.

SUMMARY OF THE INVENTION

In one aspect, the present invention provides a method of determining the stoichiometry of protein components of a viral capsid of a viral particle, in which the method comprises: (a) subjecting a sample of viral particles to hydrophilic interaction liquid chromatography (HILIC) to separate the protein components of the viral capsid of the viral particles; (b) determining the masses of protein components of the viral capsid to identify the protein components separated by HILIC; and (c) determining the relative abundance of the protein components of the viral capsid from the HILIC separation, thereby determining the stoichiometry of protein components of a viral capsid of a viral particle.

In another aspect, the present invention provides a method of determining the heterogeneity of proteins in a capsid of a viral particle, in which the method comprises: (a) subjecting the viral particle to HILIC to separate protein components of the viral particle capsid; (b) determining the masses of protein components of the protein capsid; and (c) comparing the determined masses of the protein components of the viral particle capsid with theoretical masses, wherein a deviation of one or more of the masses of protein components of the viral particle capsid from the theoretical masses is indicative of the capsid heterogeneity.

In some embodiments, the viral particle comprises an adeno-associated virus (AAV) particle.

In some embodiments, the protein components of the viral capsid comprise VP1, VP2 and VP3 of the AAV particle.

In some embodiments, the heterogeneity comprises one or more of mixed serotypes, variant capsids, capsid amino acid substitutions, truncated capsids, or modified capsids.

In some embodiments, the AAV particle comprises an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In some embodiments, the masses of VP1, VP2, and VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, AAVrh8 capsid, an AAV9 capsid, an AAV10 capsid, an AAV11 capsid, an AAV 12 capsid, or a variant thereof.

In some embodiments, the AAV particle comprises an AAV1 inverted terminal repeat sequence (ITR), an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV 10 ITR, an AAVrh10 ITR, an AAV11 ITR, or an AAV 12 ITR.

In some embodiments, the AAV particle has a capsid serotype selected for transduction of cells of a subject's liver.

In some embodiments, the AAV particle is a recombinant AAV (rAAV) particle.

In some embodiments, the AAV particle comprises an AAV vector encoding a heterologous transgene.

In some embodiments, the AAV particle has a capsid serotype AAV7, AAV8, or AAV9.

In some embodiments, the AAV particle has a capsid serotype AAV9.

In some embodiments, the AAV particle has a capsid serotype AAV9 and is a viral vector encoding Lysosomal Alpha Glucosidase (GAA) linked to an anti-CD63 antibody.

In some embodiments, the viral particle comprises a viral vector encoding a heterologous transgene.

In some embodiments, the viral particle belongs to a viral family selected from the group consisting of Adenoviridae, Parvoviridae, Retroviridae, Baculoviridae, and Herpesviridae.

In some embodiments, the viral particle belongs to a viral genus selected from the group consisting of *Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus,*

*Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus,* and *Rhadinovirus.*

In some embodiments, the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend virus, Murine Stem Cell Virus (MSCV) Rous Sarcoma Virus (RSV), human T cell leukemia viruses, Human Immunodeficiency Virus (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

In some embodiments, the HILIC uses a mobile phase A comprising trifluoroacetic acid in water.

In some embodiments, the mobile phase A comprises about 0.1% trifluoroacetic acid.

In some embodiments, the chromatography comprises a mobile phase B comprising trifluoroacetic acid in acetonitrile.

In some embodiments, the mobile phase B comprises about 0.1% trifluoroacetic acid.

In some embodiments, the proportion of mobile phase A in the chromatography increases over time.

In some embodiments, the mobile phase A increases from about 15% to about 100%, over about 45 minutes.

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

MS/MS: Tandem Mass Spectrometry
MS: Mass Spectrometry
ITRs: Inverted Terminal Repeat Sequences
rAAV vector: Recombinant AAV Vector
HILIC: Hydrophilic Interaction Liquid Chromatography
GAA: Lysosomal Alpha Glucosidase
mAb: Monoclonal Antibody
IgG: Immunoglobulin G
LC: Light Chain
HC: Heavy Chain
AAV: Adeno-Associated Virus
PTMs: Post-translational Modifications
ERT: enzyme replacement therapy Definitions "Adeno-associated virus" or "AAV": AAV is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the *Dependovirus* genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

Figures 2A, 2B:
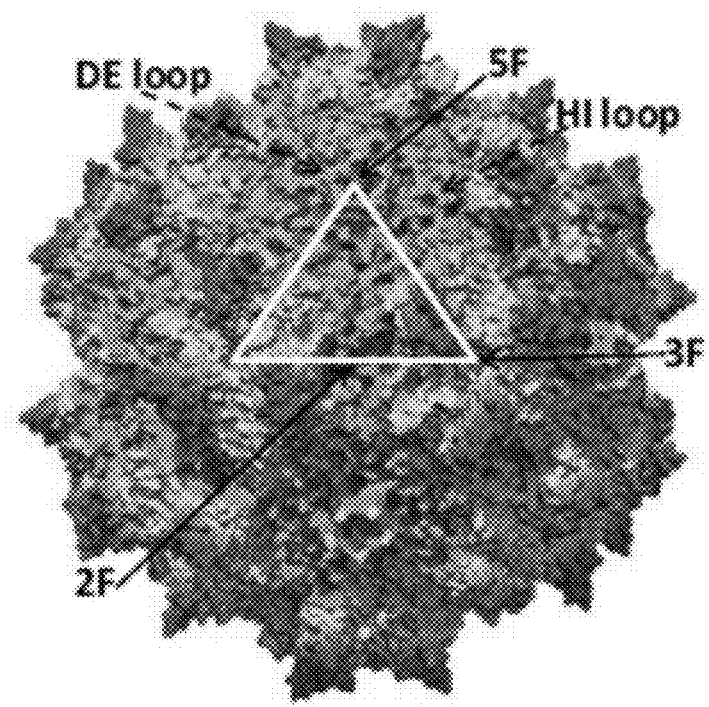
FIG. 2A is a model of an AAV viral capsid.
FIG. 2B is schematic representation of the viral capsid proteins from an AAV serotype and their approximate masses.

The Rep gene is transcribed from promoters p5 and p19 into four Rep proteins (Rep78, Rep68, Rep52, and Rep40), which have important roles in the life cycle of the virus. Proteins Rep78 and Rep68 are encoded by the mRNA transcribed from promoter p5. These proteins are essential for viral DNA replication, transcription and control of site-specific integration. The two smaller proteins Rep52 and Rep40 are generated by the mRNA transcribed from promoter p19. These proteins are involved in the formation of a single-stranded viral genome for packaging and viral integration. The Cap gene encodes three viral capsid proteins: VP1 (735 amino acids, ~90 kDa), VP2 (598 amino acids, ~72 kDa) and VP3 (533 amino acids, ~60 kDa), which form the viral capsid of 60 subunits, at the ratio of 1:1:10 (see FIGS. 2A and 2B). The three capsid proteins are translated from the mRNA transcribed from the promoter p40.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains*, 27(1) Dev. Comp. Immunol. 55-77 (2003); and M. Potter, *Structural correlates of immunoglobulin diversity*, 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527(Dec. 30, 2010).

The terms "antigen-binding portion" and "antigen-binding fragment" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germ line immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "corresponding" is a relative term indicating similarity in position, purpose or structure. A mass spectral signal due to a particular peptide or protein is also referred to as a signal corresponding to the peptide or protein. In certain embodiments, a particular peptide sequence or set of amino acids, such as a protein, can be assigned to a corresponding peptide mass.

The term "isolated," as used herein, refers to a biological component (such as a nucleic acid, peptide, protein, lipid, viral particle or metabolite) that has been substantially separated, produced apart from, or purified away from other biological components in the cell of the organism in which the component naturally occurs or is transgenically expressed.

"Mass spectrometry" is a method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), orbitrap mass analyzer, Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example HILIC.

Tandem mass spectrometry or MS/MS is a technique to break down selected ions (precursor ions) into fragments (product ions). The fragments then reveal aspects of the chemical structure of the precursor ion. In tandem mass spectrometry, once samples are ionized (for example by ESI, MALDI, EI, etc.) to generate a mixture of ions, precursor ions, for example peptides from a digest, of a specific mass-to-charge ratio (m/z) are selected (MS1) and then fragmented (MS2) to generate a product ions for detection. Typical Tandem MS instruments include QqQ, QTOF, and hybrid ion trap/FTMS, etc. One example of an application of tandem mass spectrometry is protein identification. The first mass analyzer isolates ions of a particular m/z value that represent a single species of peptide among many introduced into and then emerging from the ion source. Those ions are then accelerated into a collision cell containing an inert gas such as argon to induce ion fragmentation. This process is designated collisionally induced dissociation (CID) or collisionally activated dissociation (CAD). The m/z values of fragment ions are then measured in a $2^{nd}$ mass analyzer to obtain amino acid sequence information. Tandem mass spectrometry can be used to identify the sequence of a peptide and hence full or partial length proteins according to the methods disclosed herein. Precursor ions can be activated (with increased internal energy) in many different ways. Fragmentation patterns depend on how energy is transferred to the precursor ion, the amount of energy transferred, and how the transferred energy is internally distributed. Collision-induced dissociation and infrared multiphoton dissociation are "slow-heating" techniques that increase the Boltzmann temperature of the ion and thus preferentially cleave the weakest bonds.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I Ile; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr.

References to a mass of an amino acid means the monoisotopic mass or average mass of an amino acid at a given isotopic abundance, such as a natural abundance. In some examples, the mass of an amino acid can be skewed, for example, by labeling an amino acid with an isotope. Some degree of variability around the average mass of an amino acid is expected for individual single amino acids based on the exact isotopic composition of the amino acid. The masses, including monoisotopic and average masses for amino acids are easily obtainable by one of ordinary skill the art.

Similarly, references to a mass of a peptide or protein means the monoisotopic mass or average mass of a peptide or protein at a given isotopic abundance, such as a natural abundance. In some examples, the mass of a peptide can be skewed, for example, by labeling one or more amino acids in the peptide or protein with an isotope. Some degree of variability around the average mass of a peptide is expected for individual single peptides based on the exact isotopic composition of the peptide. The mass of a particular peptide can be determined by one of ordinary skill the art.

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups.

Alternatively, the backbone of the nucleic acid can comprise a polymer of synthetic subunits such as phosphoramidates and thus can be an oligodeoxynucleoside phosphoramidate (P-NH2) or a mixed phosphoramidate-phosphodiester oligomer. In addition, a double-stranded nucleic acid can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

A "recombinant viral vector" refers to a recombinant polynucleotide vector including one or more heterologous sequences (i.e., nucleic acid sequence not of viral origin).

A "recombinant AAV vector (rAAV vector)" refers to a polynucleotide vector including one or more heterologous sequences (i.e., nucleic acid sequence not of AAV origin) that may be flanked by at least one, e.g., two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins).

A "viral particle" refers to a viral particle composed of at least one viral capsid protein and an encapsulated viral genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral vector is a heterologous nucleotide sequence with respect to the vector.

An "inverted terminal repeat" or "ITR" sequence is relatively short sequences found at the termini of viral genomes which are in opposite orientation. An "AAV inverted terminal repeat (ITR)" sequence, is an approximately 145-nucleotide sequence that is present at both termini of a single-stranded AAV genome.

The term "hydrophilic interaction chromatography" or HILIC is intended to include a process employing a hydrophilic stationary phase and a hydrophobic organic mobile phase in which hydrophilic compounds are retained longer than hydrophobic compounds. In certain embodiments, the process utilizes a water-miscible solvent mobile phase.

The term "sample," as used herein, refers to a mixture of molecules that comprises at least a viral particle, such as an AAV particle, that is subjected to manipulation in accordance with the methods of the invention, including, for example, separating, analyzing, extracting, concentrating, profiling and the like.

The term "chromatographic surface," as used herein, includes a surface which is exposed to a sample or analytes. A chromatographic surface can be chemically modified, functionalized or activated or have a microstructure, e.g. a pore. In certain embodiments, the chromatographic surface can be hydrophobic, hydrophilic (polar) or ionic. In other embodiments, the chromatographic surface is fully porous, superficially porous or non-porous.

The term "chromatographic core," as used herein, includes a chromatographic material, including but not limited to an organic material such as silica, in the form of a particle, a monolith or another suitable structure, which forms an internal portion of the materials of the invention.

In certain aspects, the surface of the chromatographic core represents the chromatographic surface, or represents a material encased by a chromatographic surface, as defined herein. The chromatographic surface material may be disposed on or bonded to or annealed to the chromatographic core in such a way that a discrete or distinct transition is discernible or may be bound to the chromatographic core in such a way as to blend with the surface of the chromatographic core resulting in a gradation of materials and no discrete internal core surface. In certain aspects, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability.

The term "hydrophilic," as used herein, describes having an affinity for, attracting, adsorbing or absorbing water.

The term "hydrophobic," as used herein, describes lacking an affinity for, repelling, or failing to adsorb or absorb water.

"Chromatography," as used herein, refers to the process of separating a mixture, for example a mixture containing viral capsid proteins. It involves passing a mixture through a stationary phase, which separates molecules of interest from other molecules in the mixture and allows one or more molecules of interest to be isolated. An example of a method of chromatographic separation is hydrophilic interaction liquid chromatography (HILIC).

"Contacting," as used herein, includes bringing together at least two substances in solution or solid phase, for example contacting a stationary phase of a chromatography material with a sample, such as a sample comprising viral particles.

General Description

Pompe disease is an autosomal recessive lysosomal storage disorder caused by mutations in the GAA gene encoding acid α-glucosidase (GAA)—a lysosomal enzyme responsible for the hydrolysis of glycogen to glucose. Deficiency in GAA results in accumulation of glycogen in lysosomes and subsequent cellular dysfunction in cardiac, skeletal, and smooth muscles as well as in the central nervous system. Pompe disease can present early in life as infantile onset Pompe disease (IOPD) or later in childhood to adulthood as late onset Pompe disease (LOPD). Respiratory failure is a prominent cause of death in both types of Pompe disease.

Figure 1:
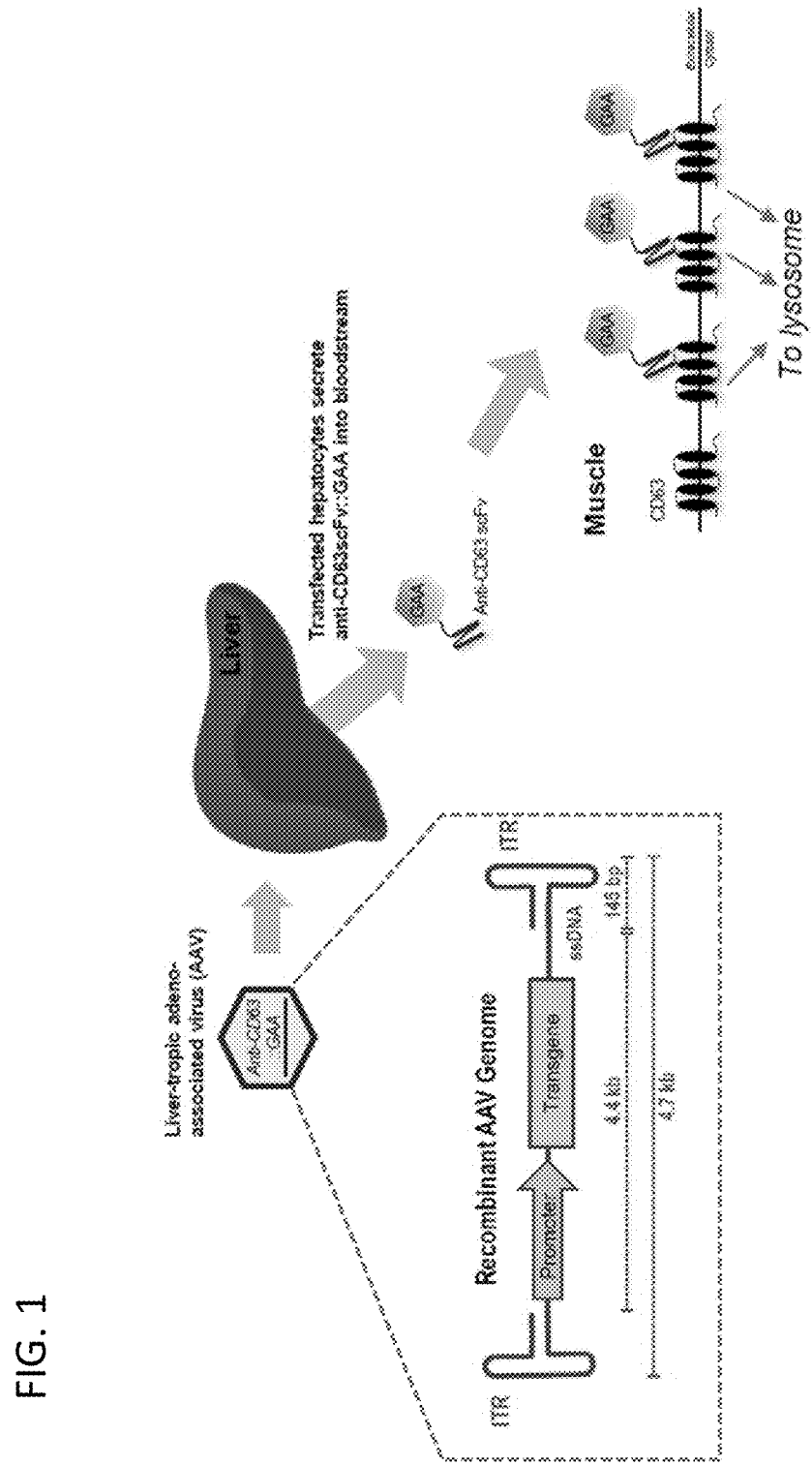
FIG. 1 is a schematic model of a possible treatment regimen for Pompe disease that includes the use of a Adeno-Associated Virus (AAV) as a Vector for Gene Therapy.

Currently, the only Food and Drug Administration approved treatment for Pompe disease is enzyme replacement therapy (ERT). However, systemically administered GAA does not cross the blood-brain barrier and therefore cannot treat the CNS pathology and affected respiratory motor neurons. Furthermore, ERT only partially corrects skeletal muscle abnormalities as a result of low uptake into muscle fibers. Consequently, two-thirds of IOPD patients eventually require ventilator support, and respiratory insufficiency persists among LOPD patients Gene therapy using adeno-associated virus (AAV) vectors is ideal for Pompe disease, since it is a monogenetic disorder. One of the strategies that is being studied is the combination of enzyme replacement with linked antibodies. In one example, high expression of anti-CD63::GAA from the liver via gene therapy is being developed to overcome the immune response to replacement enzyme seen in patients with no endogenous enzyme (see FIG. 1). As with all viral vector systems, it is important to insure that the therapeutic composition contains the right amount of correctly formed viral particles. Thus, determining stoichiometry and protein composition of viral particles is very important Aspects of this disclosure are directed to a method of determining the stoichiometry of protein components of a viral capsid of a viral particle. In embodiments, the method includes subjection a sample of viral particles to hydrophilic interaction liquid chromatography (HILIC) to separate the protein components of the viral capsid of the viral particles, such as viral particles of interest where information about the capsid is desired. In embodiments, an HILIC column is contacted with the sample containing the viral particles. In certain embodiments the method includes determining the masses of protein components of the viral capsid to identify the protein components separated by HILIC, for example, using mass spectrometry techniques, such as those described herein. In embodiments, the method includes calculating the relative abundance of the protein components of the viral capsid from the HILIC separation to determine the stoichiometry of protein components of a viral capsid of a viral particle, for example using ultraviolet (UV) detection of the protein components of the viral capsid as they are eluted from the HILIC column. For example, the area of a UV peak can be used to determine the relative abundance of the capsid proteins and used to calculate the stoichiometry of the capsid proteins in the vital capsid (see, FIG. 4). In another example, the peak height and/or peak UV intensity is used to determine relative abundance. In some embodiments, the retention time of the different proteins on the HILIC column is determined as a function of the mobile phase used and, in subsequent analysis this retention time can be used to determine the proteins and relative abundance of the proteins from the viral particle without the need to determine the mass and/or identity of the proteins every time a determination of stoichiometry is made, e.g. a standard value or values can be developed. Prior to this disclosure it was very difficult to resolve the different capsid proteins using conventional chromatography techniques (see FIGS. 3A and 3B). Using the sample conditions discussed herein for HILIC, good separation was achieved for AAV viral particles. In addition, the use of the HILIC column removed any requirement for a denaturation step. In certain embodiments, the method is used to determine the serotype of a viral particle. For example, the masses of VP 1, VP2 and VP3 of each AAV serotype are unique and can be used to identify or differentiate AAV capsid serotypes. In addition, the separated capsid proteins can be subjected to downstream analysis, such as a determination of protein sequence and post-translational modifications of the capsid proteins, for example with accurate mass measurement at the intact protein level.

Aspects of this disclosure are directed a method of determining the heterogeneity of protein components in a capsid of a viral particle. In embodiments, the method includes subjecting the viral particle to HILIC to separate protein components of the viral particle capsid. In embodiments, the method includes determining the masses of protein components of the protein capsid. In some cases, the masses of the protein components of the viral particle capsid are compared with theoretical masses of the viral particle capsid. A deviation of one or more of the masses of protein components of the viral particle capsid indicates that one or more proteins of the capsid are heterogeneous (see FIG. 5A). Conversely, no deviation would indicate that the proteins of the capsid are homogeneous (see FIG. 5B-5D). In embodiments, heterogeneity is due to one or more of mixed serotypes, variant capsids, capsid amino acid substitutions, truncated capsids, or modified capsids. In some embodiments, the determination of the stoichiometry of protein components of a viral capsid of a viral particle and the determination of the heterogeneity of protein components in a capsid of a viral particle are done on the same sample, for example is a single test.

In certain embodiments, the viral particle is an adeno-associated virus (AAV) particle and the methods disclosed can be used to determine the stoichiometry of protein components in a capsid of an AAV particle and/or heterogeneity of protein components in a capsid of a AAV particle. In embodiments, the protein components of the protein capsid comprise VP1, VP2 and VP3 of an AAV particle. In embodiments, the AAV particle is a recombinant AAV (rAAV) particle. In embodiments, the AAV particle includes an AAV vector encoding a heterologous transgene. In some embodiments, a determined or calculated mass of the present disclosure (e.g., the determined or calculated mass of VP1, VP2 and/or VP3 of the AAV particle) may be compared with a reference, for example, a theoretical mass of a VP1, VP2, and/or VP3 of one or more AAV serotypes (see, for example, FIGS. 2A and 2B). A reference may include a theoretical mass of a VP1, VP2, and/or VP3 of one or more of any of the AAV serotypes. For example, in some embodiments, the masses of VP1, VP2, and/or VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV 10 capsid, an AAV 11 capsid, an AAV 12 capsid, or a variant thereof. In some embodiments, a determined or calculated mass (e.g., the determined or calculated mass of VP1, VP2 and/or VP3 of the AAV particle) may be compared with a theoretical mass of a VP1, VP2, and/or VP3 of the corresponding AAV serotype.

In some embodiments, the methods of the present disclosure may include determining the heterogeneity of the proteins of an AAV particle. In some embodiments, a deviation of one or more of the masses of VP1, VP2 and/or VP3 (e.g., from a reference mass, such as a theoretical, predicted, or expected mass) is indicative of the AAV capsid protein heterogeneity. In some embodiments, heterogeneity may include one or more of the following, without limitation: mixed serotypes, variant capsids, capsid amino acid substitutions, truncated capsids, or modified capsids.

In some embodiments, a method of determining the heterogeneity of an AAV particle may include subjecting a denatured AAV particle to LC/MS (e.g., as described herein), determining the masses of VP1, VP2 and VP3 of the AAV particle, and comparing these masses with theoretical masses of VP1, VP2 and VP3 of the AAV serotype; as well as subjecting fragments of VP1, VP2 and/or VP3 to LC/MS/MS, determining the masses of fragments of VP1, VP2 and VP3 of the AAV particle, and comparing these masses with theoretical masses of VP1, VP2 and VP3 of the AAV serotype (a deviation of one or more of the masses of VP1, VP2 or VP3 are indicative of the AAV capsid heterogeneity).

In embodiments, the AAV particle includes an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In embodiments, the masses of VP1, VP2, and VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In embodiments, the AAV particle comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV 10 ITR, an AAV11 ITR, or an AAV 12 ITR.

In embodiments, the AAV particle has a capsid serotype selected for transduction of cells of a subject's liver. In embodiments, the AAV particle has a capsid serotype AAV7, AAV8, or AAV9, which are selective for the transduction of cells of a subject's liver.

In some embodiments, the AAV particle is a recombinant AAV (rAAV) particle. In some embodiments, the AAV particle comprises an AAV vector encoding a heterologous transgene. In some embodiments, the AAV particle has a capsid serotype AAV7, AAV8, or AAV9. In some embodiments, the AAV particle has a capsid serotype AAV9. In some embodiments, the AAV particle has a capsid serotype AAV9 and is a viral vector encoding Lysosomal Alpha Glucosidase (GAA) linked to an antibody specific for an antigen expressed from a muscle cell (e.g., an anti-CD63 antibody).

While AAV was the model viral particle for this disclosure, it is contemplated that the disclosed methods can be applied to profile a variety of viruses, e.g., the viral families, subfamilies, and genera. The methods of the present disclosure may find use, e.g., in profiling VPs to monitor VP expressions, posttranslational modifications, and truncations and to ensure product consistency during VLP production, to confirm site-direct mutagenesis or structural characterization for capsid protein engineering applications, and/or to monitor or detect heterogeneity of a viral particle or preparation.

In embodiments, the viral vector encodes a heterologous transgene.

In embodiments, the viral particle belongs to a viral family selected from the group consisting of Adenoviridae, Parvoviridae, Retroviridae, Baculoviridae, and Herpesviridae.

In embodiments, the viral particle belongs to a viral genus selected from the group consisting of *Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus,* and *Rhadinovirus*.

In embodiments, the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend virus, Murine Stem Cell Virus (MSCV) Rous Sarcoma Virus (RSV), human T cell leukemia viruses, Human Immunodeficiency Viruse (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

Hydrophilic interaction chromatography (HILIC) is a variant of NP-HPLC that can be performed with partially aqueous mobile phases, permitting normal-phase separation of peptides, carbohydrates, nucleic acids, and many proteins. The elution order for HILIC is least polar to most polar, the opposite of that in reversed-phase HPLC.

HILIC separates analytes based on polar interactions between the analytes and the stationary phase (e.g., substrate). The polar analyte associates with and is retained by the polar stationary phase. Adsorption strengths increase with increases in analyte polarity, and the interaction between the polar analyte and the polar stationary phase (relative to the mobile phase) increases the elution time. Use of more polar solvents in the mobile phase will decrease the retention time of the analytes, while more hydrophobic solvents tend to increase retention times.

Various types of substrates can be used with HILIC, e.g., for column chromatography, including silica, amino, amide, cellulose, cyclodextrin and polystyrene substrates. Examples of useful substrates, e.g., that can be used in column chromatography, include: polySulfoethyl Aspartamide (e.g., from PolyLC), a sulfobetaine substrate, e.g., ZIC®-HILIC (e.g., from SeQuant), POROS® HS (e.g., from Applied Biosystems), POROS® S (e.g., from Applied Biosystems), PolyHydroethyl Aspartamide (e.g., from PolyLC), Zorbax 300 SCX (e.g., from Agilent), PolyGLYCOPLEX® (e.g., from PolyLC), Amide-80 (e.g., from Tosohaas), TSK GEL® Amide-80 (e.g., from Tosohaas), Polyhydroxyethyl A (e.g., from PolyLC), Glyco-Sep-N (e.g., from Oxford GlycoSciences), and Atlantis HILIC (e.g., from Waters). Columns that can be used in the disclosed methods include columns that utilize one or more of the following functional groups: carbamoyl groups, sulfopropyl groups, sulfoethyl groups (e.g., poly (2-sulfoethyl aspartamide)), hydroxyethyl groups (e.g., poly (2-hydroxyethyl aspartamide)) and aromatic sulfonic acid groups.

In certain embodiments, the capsid proteins are separated on the HILIC column and subsequently eluted from the HILIC column, for example using a mobile phase gradient to resolve the individual capsid proteins, thereby purifying and or separating capsid proteins in the sample. In certain examples, the eluted capsid proteins from the HILIC column are separated into one or more fractions. Such fractions can be used for subsequent analysis, such as MS analysis. In certain embodiments, the methods include identifying capsid proteins present in one or more of the fractions.

The mobile phase used may include buffers with and without ion pairing agents, e.g., acetonitrile and water. Ion pairing agents include formate, acetate, TFA and salts. Gradients of the buffers can be used, e.g., if two buffers are used, the concentration or percentage of the first buffer can decrease while the concentration or percentage of the second buffer increases over the course of the chromatography run. For example, the percentage of the first buffer can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% over the course of the chromatography run. As another example, the percentage of the second buffer can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% over the course of the same run. In embodiments, the proportion of mobile phase A in the chromatography increases over time. Optionally, the concentration or percentage of the first and second buffer can return to their starting values at the end of the chromatography run. As an example, the percentage of the first buffer can change in five steps from 85% to 63% to 59% to 10% to 85%; while the percentage of the second buffer in the same steps changes from 15% to 37% to 41% to 90% to 15%. The percentages can change gradually as a linear gradient or in a non-linear (e.g., stepwise) fashion. For example, the gradient can be multiphasic, e.g., biphasic, triphasic, etc. In preferred embodiments, the methods described herein use a decreasing acetonitrile buffer gradient which corresponds to increasing polarity of the mobile phase without the use of ion pairing agents. In embodiments, the HILIC uses a mobile phase A comprising trifluoroacetic acid in water. In embodiments, the mobile phase A comprises about 0.1% trifluoroacetic acid. In embodiments, the chromatography comprises a mobile phase B comprising trifluoroacetic acid in acetonitrile. In embodiments, the mobile phase B comprises about 0.1% trifluoroacetic acid.

The column temperature can be maintained at a constant temperature throughout the chromatography run, e.g., using a commercial column heater. In some embodiments, the column is maintained at a temperature between about 50° C. to about 70° C., e.g., about 50° C. to about 60° C., about 55° C. to about 60° C., e.g., at about 50° C., about 55° C., about 60° C., about 65° C., or about 70° C. In one embodiment, the temperature is about 60° C.

The flow rate of the mobile phase can be between about 0 to about 100 ml/min. For analytical proposes, flow rates typically range from 0 to 10 ml/min, for preparative HPLC, flow rates in excess of 100 ml/min can be used. For example, the flow rate can be about 0.5, about 1, about 1.5, about 2, about 2.5, about 3, about 3.5, about 4, about 4.5, or about 5 ml/min. Substituting a column having the same packing, the same length, but a smaller diameter requires a reduction in the flow rate in order to maintain the same retention time and resolution for peaks as seen with a column of wider diameter. Preferably, a flow rate equivalent to about 1 ml/min in a 4.6×100 mm, 5 μm column is used.

The run time can be between about 15 to about 240 minutes, e.g., about 20 to about 70 min, about 30 to about 60 min, about 40 to about 90 min, about 50 min to about 100 min, about 60 to about 120 min, about 50 to about 80 min. In embodiments, the mobile phase A increases from about 15% to about 100%, over about 45 minutes.

In some embodiments, the methods include subjecting a viral particle to liquid chromatography/mass spectrometry (LC/MS). As is known in the art, LC/MS utilizes liquid chromatography for physical separation of ions and mass spectrometry for generation of mass spectral data from the ions. Such mass spectral data may be used to determine, e.g., molecular weight or structure, identification of particles by mass, quantity, purity, and so forth. These data may represent properties of the detected ions such as signal strength (e.g., abundance) over time (e.g., retention time), or relative abundance over mass-to-charge ratio.

In some embodiments, mass spectrometry (e.g., used in LC/MS as described herein) may refer to electrospray ionization mass spectrometry (ESI-MS). ESI-MS is known in the art as a technique that uses electrical energy to analyze ions derived from a solution using mass spectrometry (see, e.g., Yamashita, M. and Fenn, J. B. (1984). Phys. Chem. 88:4451-4459). Ionic species (or neutral species that are ionized in solution or in gaseous phase) are transferred from a solution to a gaseous phase by dispersal in an aerosol of charged droplets, followed by solvent evaporation that reduces the size of the charged droplets and sample ion ejection from the charge droplets as the solution is passed through a small capillary with a voltage relative to ground (e.g., the wall of the surrounding chamberESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the capillary into an electrospray nozzle, e.g., the capillary functions as the sample loader. In another embodiment, the capillary itself functions as both the extraction device and the electrospray nozzle.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one embodiment, the eluted sample is deposited directly from the capillary onto the metal target, e.g., the capillary itself functions as the sample loader. In one embodiment, the extracted analyte is deposited on a MALDI target, a MALDI ionization matrix is added, and the sample is ionized and analyzed, e.g., by TOF detection.

In some embodiments, other ionization modes are used e.g. ESI-MS, turbospray ionization mass spectrometry, nanospray ionization mass spectrometry, thermospray ionization mass spectrometry, sonic spray ionization mass spectrometry, SELDI-MS and MALDI-MS. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt. In the case of MALDI, the analyte should be in a solvent compatible with spotting on the target and with the ionization matrix employed.

In some embodiments, the methods include subjecting a viral particle of the present disclosure, or subjecting digested fragments of a denatured viral particle of the present disclosure, to liquid chromatography/mass spectrometry-mass spectrometry (LC/MS/MS). As is known in the art, LC/MS/MS (the term "liquid chromatography-tandem mass spectrometry" may be used interchangeably herein) utilizes liquid chromatography for physical separation of ions and mass spectrometry for generation of mass spectral data from the ions, where the mass spectrometry uses multiple stages of mass (e.g., m/z) separation, typically separated by a fragmentation step. For example, ions of interest within a range of m/z may be separated out in a first round of MS, fragmented, and then further separated based on individual m/z in a second round of MS. Ion fragmentation may include without limitation a technique such as collision-induced dissociation (CID), higher energy collision dissociation (HCD), electron-capture dissociation (ECD), or electron-transfer dissociation (ETD).

A variety of mass analyzers suitable for LC/MS and/or LC/MS/MS are known in the art, including without limitation time-of-flight (TOF) analyzers, quadrupole mass filters, quadrupole TOF (QTOF), and ion traps (e.g., a Fourier transform-based mass spectrometer or an Orbitrap). In Orbitrap, a barrel-like outer electrode at ground potential and a spindle-like central electrode are used to trap ions in trajectories rotating elliptically around the central electrode with oscillations along the central axis, confined by the balance of centrifugal and electrostatic forces. The use of such instruments employs a Fourier transform operation to convert a time domain signal (e.g., frequency) from detection of image current into a high resolution mass measurement (e.g., nano LC/MS/MS). Further descriptions and details may be found, e.g., in Scheltema, R. A. et al. (2014) Mol. Cell Proteomics 13:3698-3708; Perry, R. H. et al. (2008) Mass. Spectrom. Rev. 27:661-699; and Scigelova, M. et al. (2011) Mo/. Cell Proteomics 10:M11 1.009431.

In some embodiments, masses of viral capsid proteins may be determined, e.g., based on LC/MS and/or LC/MS/MS data. In some embodiments, masses of VP1, VP2 and VP3 of an AAV particle, or of fragments of VP1, VP2 and VP3 of the AAV particle, may be determined, e.g., based on LC/MS and/or LC/MS/MS data. Various methods to determine protein mass and/or identity from MS data are known in the art. For example, peptide mass fingerprinting may be used to determine protein sequence based on MS data, or proteins may be identified based on MS/MS data related to one or more constituent peptides. When using tandem MS, product ion scanning may be used to analyze m/z data related to one or more peptides of a protein of interest. Software known in the art may then be used, e.g., to match identified peaks to reference or known peaks, to group peaks into isotopomer envelopes, and so forth. Peptide mass values may be compared to a database of known peptide sequences. For example, Mascot may be used to match observed peptides with theoretical database peptides, e.g., resulting from application of a particular digest pattern to an in silico protein database. Other suitable software may include without limitation Proteome Discoverer, ProteinProspector, X! Tandem, Pepfinder, Bonics, or MassLynx™ (Waters).

In some embodiments, the heterologous nucleic acid is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., Gene, 1991, 108(2): 193-9) and the elongation factor 1- alpha promoter (EFI-alpha) promoter (Kim et al., Gene, 1990, 91(2):217-23 and Guo et al., Gene Ther., 1996, 3(9): 802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides a recombinant vector comprising a nucleic acid encoding a heterologous transgene of the present disclosure operably linked to a CBA promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the 13-actin promoter, the phosphoglycerol kinase (PGK) promoter, and the EFIa promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268: 1766-1769 (1995), see also Harvey et al., Curr. Opin. Chem. Biol., 2:512-518 (1998)), the RU486-inducible system (Wang et al., Nat. Biotech., 15:239-243 (1997) and Wang et al, Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art.

In some embodiments, the vector comprises an intron. For example, in some embodiments, the intron is a chimeric intron derived from chicken beta-actin and rabbit beta-globin. In some embodiments, the intron is a minute virus of mice (MVM) intron.

In some embodiments, the vector comprises a polyadenylation (polyA) sequence. Numerous examples of polyadenylation sequences are known in the art, such as a bovine growth hormone (BGH) Poly(A) sequence (see, e.g., accession number EF592533), an SV40 polyadenylation sequence, and an HSV TK pA polyadenylation sequence.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the examples described herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

The following examples are provided to illustrate particular features of certain embodiments. However, the particular features described below should not be considered as limitations on the scope of the invention, but rather as examples from which equivalents will be recognized by those of ordinary skill in the art.

EXAMPLE

The following example is put forth so as to provide those of ordinary skill in the art with a complete disclosure and description of how to make and use the methods of the invention, and is not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight unless indicated, temperature is in degrees Centigrade, room temperature is about 25° C., and pressure is at or near atmospheric.

Separation of Capsid Proteins From Intact AAV Particles

Figure 4:
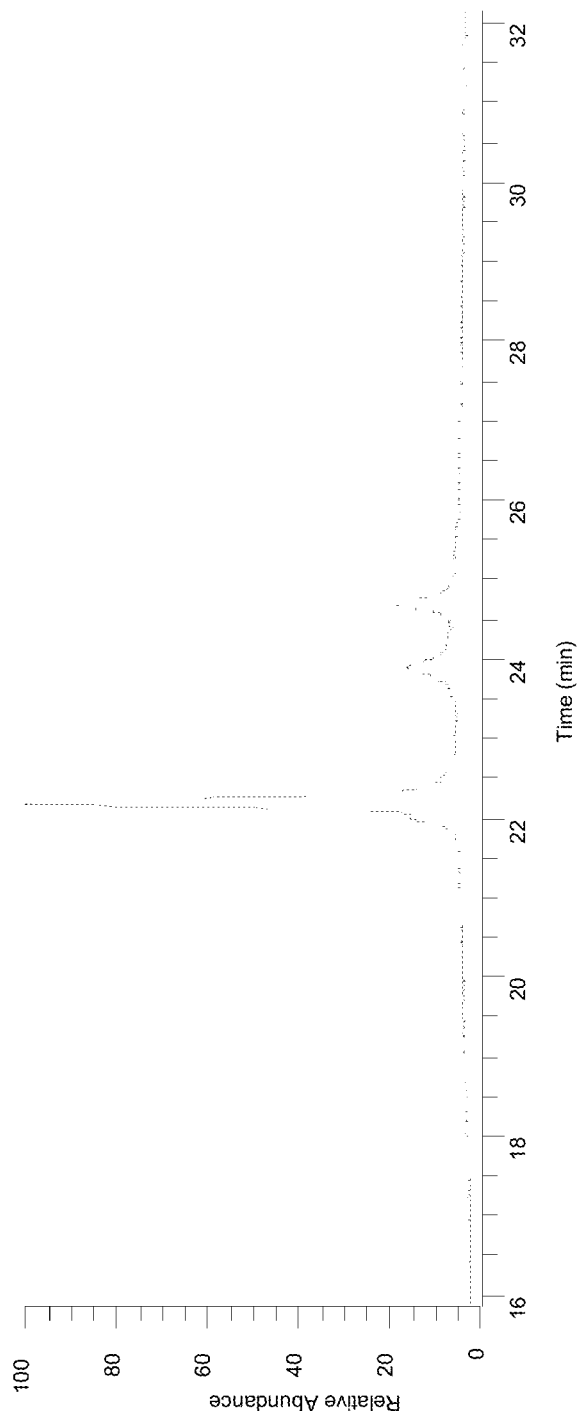
FIG. 4 is UV trace from a hydrophilic interaction liquid chromatography (HILIC) separation of AAV capsid proteins from an AAV particle showing high resolution of the individual proteins and the determination of the relative abundance of the individual proteins.

For separation of an intact AAV9 viral particles, 1 µL of the AAV sample was injected onto a HILIC column, as described in the table below. The results of the separation are shown in FIG. 4. As shown, the three AAV capsid proteins showed complete resolution from each other.

Table 1 shows a summary of the chromatographic conditions used for the separation of AAV9 capsid proteins from an intact AAV9 capsid.

TABLE 1

Summary of chromatographic conditions

| | | | |
|---|---|---|---|
| UPLC System | Waters ACQUITY UPLC I-Class | | |
| Mobile Phase | A: 0.1% TFA in water | | |
| | B: 0.1% TFA in acetonitrile | | |
| Column | ACQUITY UPLC ® Glycoprotein BEH Amide 1.7 µm, 2.1 mm × 150 mm, Part No. 186007963 | | |
| Column Temperature | 60° C. ± 1° C. | | |
| Autosampler Temperature | 5° C. ± 2° C. | | |
| Gradient | Time (min) | Flow (mL/min) | % A | % B |
| | 0 | 0.2 | 15.0 | 85.0 |
| | 0.5 | 0.2 | 15.0 | 85.0 |
| | 1.0 | 0.2 | 25.0 | 75.0 |
| | 41.0 | 0.2 | 40.0 | 60.0 |
| | 42.0 | 0.2 | 100.0 | 0.0 |

TABLE 1-continued

| Summary of chromatographic conditions | | | | |
|---|---|---|---|---|
| | 44.0 | 0.2 | 100.0 | 0.0 |
| | 45.0 | 0.2 | 15.0 | 85.0 |
| | 55.0 | 0.2 | 15.0 | 85.0 |
| Detector Wavelength | 280 nm | | | |

Figure 3A:
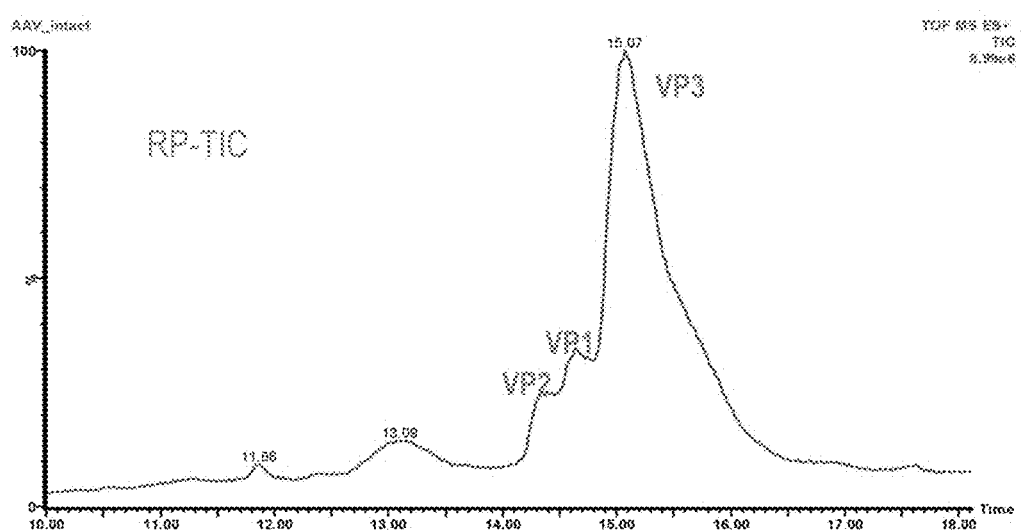
FIG. 3A is UV trace from a reverse phase TIC separation of AAV capsid proteins from an AAV particle showing poor resolution of the individual proteins.
Figure 3B:
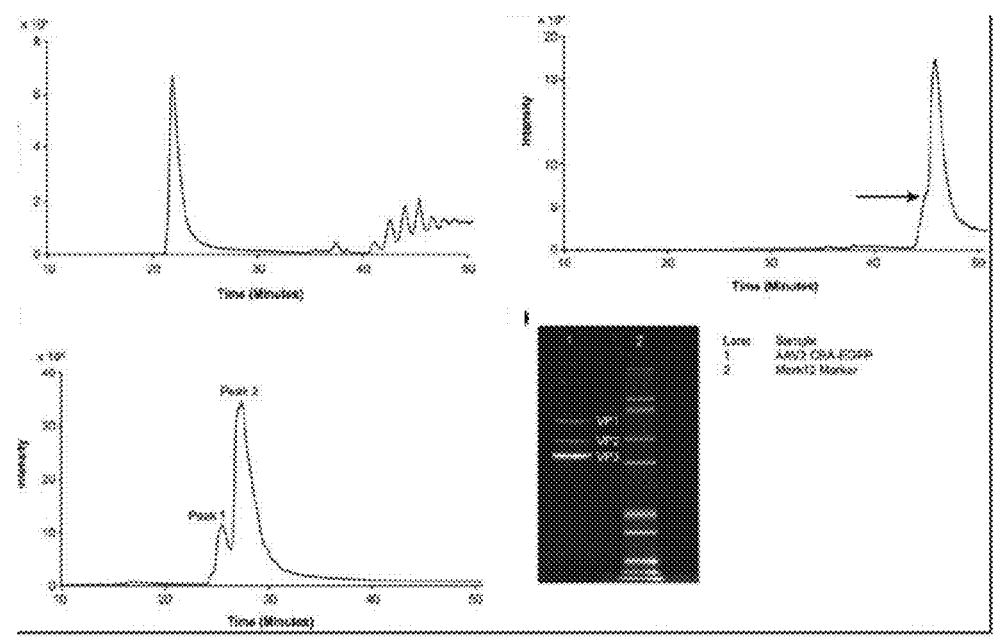
FIG. 3B is a comparison of several prior art separation methods showing both poor resolution and/or poor quantification.

Compared to RP-based separation, the unique retention mechanism of the HILIC column worked surprisingly better for VP separation (see FIGS. 4, 3A and 3B).

Mass Spectral Analysis of Separated AAV Capsid Proteins

One of the advantages of the methods described herein is that no sample preparation is required. 1 uL of the sample was directly injected into the into the LC-MS and the resulting data analyzed. The following tune parameters were applied on a Q-Exactive Plus mass spectrometer for intact mass analysis:

| | |
|---|---|
| Spray voltage | 3.5 kV |
| Capillary Temperature | 350° C. |
| S-lens RF level | 60 |
| Sheath Gas flow rate | 40 |
| Aux Gas flow rate | 15 |
| In-source CID | 0.0 eV |
| m/z range | 800-4000 |

Figures 5A, 5B, 5C, 5D:
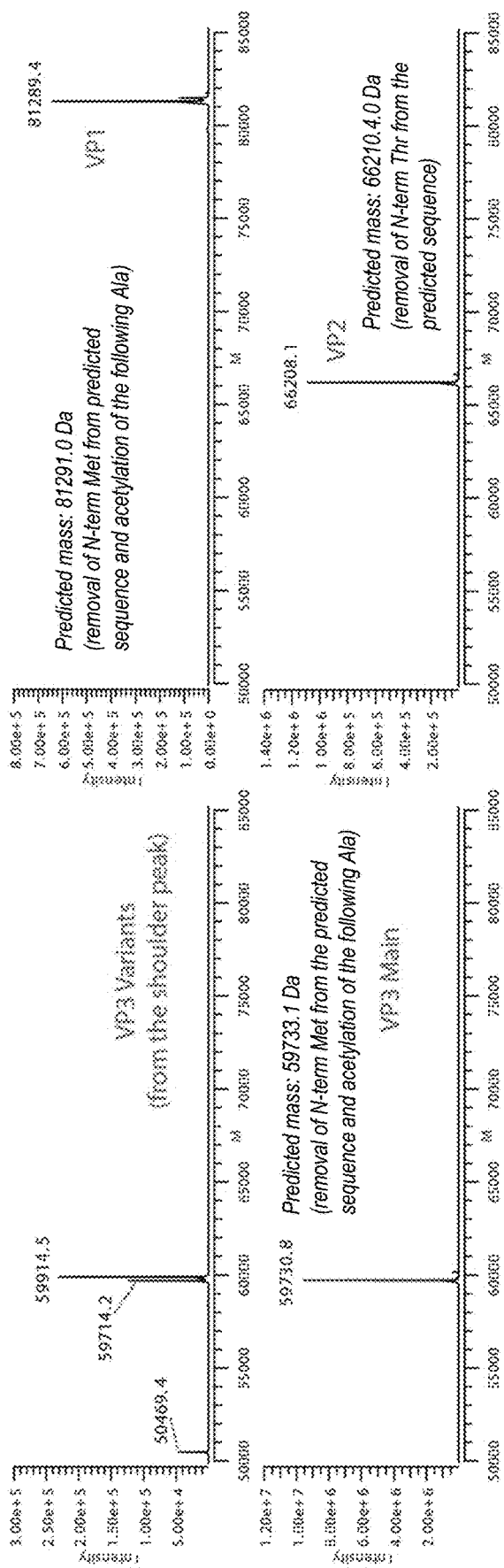
FIGS. 5A-5D are mass spectra of AAV capsid proteins from an AAV particle.

FIGS. 5A-5D show mass spectra of the individual capsid proteins. As shown in FIG. 5A, there was protein heterogeneity in VP3.

Figure 6:
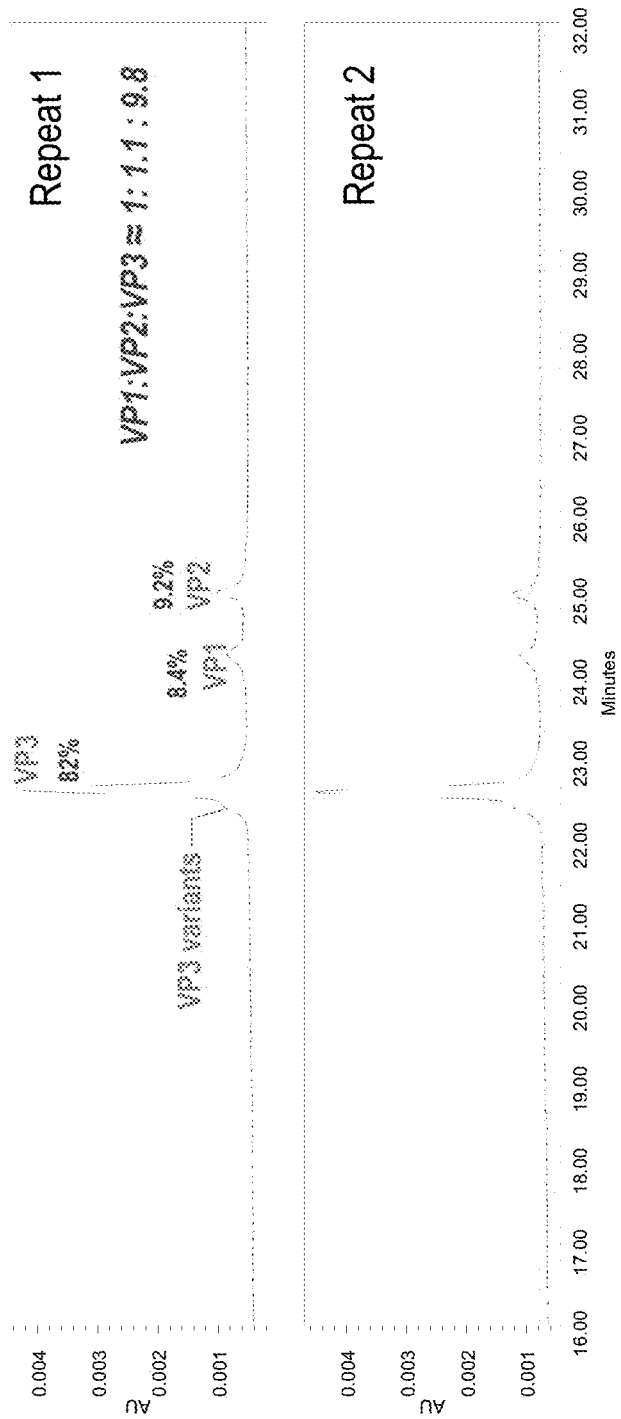
FIG. 6 shows two traces of HILIC-UV analysis of AAV9 viral particles and their stoichiometry determination.

As shown in FIG. 6, the peak height can be used to determine the stoichiometry of the intact AAV particles.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of determining the stoichiometry of protein components of an intact, non-enveloped viral particle, comprising: subjecting a sample comprising said viral particle to hydrophilic interaction liquid chromatography (HILIC) to separate the protein components of the viral capsid of the viral particle; determining the masses of protein components of the viral capsid to identify the protein components separated by HILIC; determining the relative abundance of the protein components of the viral capsid from the HILIC separation, thereby determining the stoichiometry of protein components of the viral capsid of said viral particle.

2. The method of claim 1, wherein the viral particle comprises an adeno-associated virus (AAV) particle.

3. The method of claim 2, wherein the protein components of the protein capsid comprise VP1, VP2 and VP3 of the AAV particle.

4. The method of claim 2, wherein the masses of VP1, VP2, and VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, AAVrh8 capsid, an AAV9 capsid, an AAV10 capsid, an AAV11 capsid, an AAV 12 capsid, or a variant thereof.

5. The method of claim 3, wherein the AAV particle comprises an AAV1 capsid, an AAV2 capsid, an AAV3 capsid, an AAV4 capsid, an AAV5 capsid, an AAV6 capsid, an AAV7 capsid, an AAV8 capsid, AAVrh8 capsid, an AAV9 capsid, an AAV10 capsid, an AAV11 capsid, an AAV 12 capsid, or a variant thereof.

6. The method of claim 2, wherein the AAV particle comprises an AAV1 ITR, an AAV2 ITR, an AAV3 ITR, an AAV4 ITR, an AAV5 ITR, an AAV6 ITR, an AAV7 ITR, an AAV8 ITR, an AAV9 ITR, an AAV 10 ITR, an AAV11 ITR, or an AAV 12 ITR.

7. The method of claim 2, wherein the AAV particle is a recombinant AAV (rAAV) particle or an AAV vector encoding a heterologous transgene.

8. The method of claim 2, wherein the AAV particle has a capsid serotype selected for transduction of cells of a subject's liver.

9. The method of claim 8, wherein the AAV particle has a capsid serotype AAV7, AAV8, or AAV9.

10. The method of claim 9, wherein the AAV particle has a capsid serotype AAV9.

11. The method of claim 2, wherein the AAV particle has a capsid serotype AAV9 and is a viral vector encoding Lysosomal Alpha Glucosidase (GAA) linked to an anti-CD63 antibody.

12. The method of claim 1, wherein the viral particle comprises a viral vector
encoding a heterologous transgene or belongs to a viral family selected from the group consisting of Adenoviridae, Parvoviridae, Retroviridae, Baculoviridae, and Herpesviridae.

13. The method of claim 12, wherein the viral particle belongs to a viral genus selected from the group consisting of *Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus*, and *Rhadinovirus*.

14. The method of claim 12, wherein the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend virus, Murine Stem Cell Virus (MSCV) Rous Sarcoma Virus (RSV), human T cell leukemia viruses, Human Immunodeficiency Viruse (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

15. The method of claim 1, wherein the HILIC uses a mobile phase A comprising trifluoroacetic acid in water or a mobile phase B comprising trifluoroacetic acid in acetonitrile.

16. The method of claim 13, wherein the mobile phase A or the mobile B phase comprises about 0.1% trifluoroacetic acid.

17. The method of claim 15, wherein the proportion of mobile phase A in the chromatography increases over time.

18. The method of claim 17, wherein mobile phase A increases from about 15% to about 100%, over about 45 minutes.

19. A method of determining the heterogeneity of protein components of a capsid of an intact, non-enveloped viral particle comprising: subjecting a sample comprising said viral particle to hydrophilic interaction liquid chromatography (HILIC) to separate protein components of the viral particle's capsid; determining the masses of the protein components of the capsid; comparing the determined masses of the protein components of the viral particle's capsid with theoretical masses, wherein a deviation of one or more of the masses of protein components of the viral particle's capsid from the theoretical masses is indicative of capsid heterogeneity.

20. The method of claim 19, wherein the heterogeneity comprises one or more of mixed serotypes, variant capsids, capsid amino acid substitutions, truncated capsids, or modified capsids.

* * * * *